(12) United States Patent
Gaa et al.

(10) Patent No.: US 7,736,904 B2
(45) Date of Patent: Jun. 15, 2010

(54) METHOD FOR VERIFYING FITNESS OF AN ANALYSIS ELEMENT

(75) Inventors: Otto Gaa, Worms (DE); Gertrud Albrecht, Mannheim (DE); Dieter Loch-Leroux, Carlsberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 69 days.

(21) Appl. No.: 12/020,259

(22) Filed: Jan. 25, 2008

(65) Prior Publication Data

US 2008/0138906 A1    Jun. 12, 2008

Related U.S. Application Data

(63) Continuation of application No. 10/911,336, filed on Aug. 4, 2004, now abandoned, which is a continuation of application No. 09/943,639, filed on Aug. 29, 2001, now abandoned.

(30) Foreign Application Priority Data

Sep. 1, 2000    (DE) ................. 100 43 556

(51) Int. Cl.
    *G01N 21/77* (2006.01)
(52) U.S. Cl. .................. 436/169; 436/164; 436/8
(58) Field of Classification Search .............. None
    See application file for complete search history.

(56) References Cited

U.S. PATENT DOCUMENTS

| | | |
|---|---|---|
| 4,160,646 A | 7/1979 | Furutani et al. |
| 4,436,812 A | 3/1984 | Endoh et al. |
| 4,615,462 A | 10/1986 | Sacherer et al. |
| 4,832,488 A | 5/1989 | Hirai et al. |
| 4,834,234 A | 5/1989 | Sacherer et al. |
| 4,884,213 A | 11/1989 | Iwata et al. |
| 5,174,963 A | 12/1992 | Fuller et al. |
| 5,258,308 A | 11/1993 | Freeman et al. |
| 5,277,870 A | 1/1994 | Fuller et al. |
| 5,279,294 A | 1/1994 | Anderson et al. |
| 5,645,798 A | 7/1997 | Schreiber et al. |
| 5,720,924 A | 2/1998 | Eikmeier et al. |
| 5,780,304 A | 7/1998 | Matzinger et al. |
| 6,103,536 A | 8/2000 | Geisberg |

FOREIGN PATENT DOCUMENTS

| | | |
|---|---|---|
| DE | 2800225 A1 | 7/1978 |
| DE | 19854316 A1 | 10/1999 |
| EP | 1022565 A2 | 7/2000 |

*Primary Examiner*—Yelena G Gakh
(74) *Attorney, Agent, or Firm*—Barnes & Thornburg LLP

(57) ABSTRACT

The present invention pertains to a method for verifying usability of a test element on the basis of the relation of at least one control parameter measurable from the blank test field of a test element to a standard value for the at least one control parameter. In one embodiment, the method comprises determining the deviation between a first ratio calculated from a blank-field reference value measured for the control parameter and a first standard value, and a second ratio calculated from a blank-field control value and the first standard value, and rejecting a test element if the deviation is not within a predetermined tolerance range for the deviation.

14 Claims, 1 Drawing Sheet

METHOD FOR VERIFYING FITNESS OF AN ANALYSIS ELEMENT

REFERENCE TO RELATED APPLICATIONS

The present application is a continuation of patent application Ser. No. 10/911,336, filed Aug. 4, 2004, now abandoned, which is a continuation of patent application Ser. No. 09/943,639, filed Aug. 29, 2001, now abandoned, which claims priority to German Patent Application No. 10043556.4, filed Sep. 1, 2000, which are hereby incorporated by reference in their entirety.

TECHNICAL FIELD OF THE INVENTION

The present invention relates generally to a method for verifying the usability of a test element provided for use with an evaluation unit in a sample analysis system, and more particularly to a method of verifying the usability of such a test element by determining whether the value measured for at least one control parameter measurable from and relating to the test element is within a predetermined tolerance range.

BACKGROUND

For qualitative and quantitative testing of liquid samples, particularly biological fluids from human beings and other animals, typical testing methods include chemical and biochemical techniques. These testing methods are largely performed using substrate-based test elements which provide relatively fast results. Such testing methods are commonly performed in specialized laboratories, but are also commonly performed outside the laboratory, such as by an individual consumer. Testing methods using the substrate-based test elements typically rely on specially developed dry-chemistry processes often involving complex reactions using sensitive reagents. Nevertheless, such methods are simple enough to perform that non-experts can perform them easily.

Test elements of this kind typically comprise reagents embedded in one or more test layers. A reaction sequence is initiated by bringing a test element into contact with a liquid sample.

Typical reaction sequences between the dry reagent and the liquid sample lead to a measurable change on the test element, which change is characteristic for purposes of the particular analysis, such as measuring the concentration of an analyte of interest in the liquid sample. The change is typically evaluated visually or by means of an evaluation device corresponding to the test element. Reflection photometry is one example of a kind of evaluation technique in this regard. For purposes of this disclosure, test elements may also be referred to as analysis elements.

Several different types of test elements are known, typically differentiated by the measuring principle (e.g. optical or electrochemical) and the reagents provided on the test element for performing the analysis. Other differentiations include test element structure, such as the arrangement and fabrication of the layers forming the test element. For example, strip shaped test elements (test strips) are common and typically comprise an oblong plastic strip and at least one test layer affixed to the strip. Another example of a test element is a plastic frame enframing at least one test layer.

One typical substrate-based test element known in the art is used for determining blood glucose concentration for diabetics. Another example of strip-shaped diagnostic test elements is for urine analysis, e.g. one-field or multi-field test strips and/or test papers. Test elements that are evaluated with an evaluation device configured for electrochemical or optical analysis techniques are well known in the art, and persons of ordinary skill in the art will be familiar with several various embodiments of test elements and corresponding evaluation devices.

Various environmental factors can have a negative impact on the analytic functionality of test elements. For example, light, temperature and/or humidity are factors that can damage a test element such that faulty measurement results are provided. Obviously this can have dangerous consequences for any diagnosis based upon such results, or it can render the test elements unusable.

As an example in the context of test elements configured for optical evaluation, light-sensitive, temperature-sensitive, and/or humidity-sensitive compounds are used for which the dry color, even before contacting a liquid sample, can change due to the environmental factors in such an extreme way that this can be recognized by an alert user. In that case, the test elements so affected can be manually segregated. However, such visual recognition is often difficult and may require sufficient experience of the user to make it effective. Moreover, due to the methodical difficulties with doing this, such a visual check is rarely performed or is simply forgotten, especially by non-expert users.

In order to protect test elements from light, humidity, dirt, germs, dust, as well as mechanical deterioration, and/or to store them in sterile conditions, test elements are typically packaged, either individually or in a common package or storage container. However, packaging typically does not offer 100% protection. For example, test elements can be damaged during fabrication, transport or improper storage. Furthermore, typical packaging often does very little to protect the test elements against temperature influences or against the effects of aging. For test elements stored in common packaging or containers in particular, the aging process proceeds increasingly after the package or container has been opened the first time. Thus, consideration must be paid to the fact of the aging of test elements once a package or container is opened.

In view of the foregoing, it is important to verify that a test element is in a usable condition before its use. Certain known methods have been employed for this purpose. For example, in photometric measurement systems it is known to determine the so-called dry-blank value of the test field before applying the liquid sample to be analyzed. That is, the remission value of the test field on the test element is determined without a sample present. The dry-blank (or blank-field) value is compared to a pre-determined tolerance value or tolerance range, and the test element is rejected if the dry-blank value exceeds the value or is not within the range. In such a case, the dry-blank value for remission serves as a "control parameter".

In this example, only a very inaccurate verification is possible because the measuring devices used for the evaluation of the test elements have their own unique tolerances during their manufacture, and because the differences between devices actually are amplified during their service life, e.g. due to changes in the device. This is particularly true of optical measurement devices. Changes can be caused by mechanical forces leading to mis-adjustment, aging of the illumination system (e.g. light emitting diodes), or dust deposits on the optical detection elements.

In addition to issues with the measurement devices, inaccuracy of known verification methods may also result from batch or lot fluctuations with respect to reagent and even test element fabrication, all of which influence the dry blank value. This can be overcome, however, by using batch- or lot-specific information or coding relating to the test elements that is provided to the evaluation device, such as from the test elements themselves or from their packaging.

Other methods are known for correction or adjustment of analyses of samples provided on test elements in optical systems, such as U.S. Pat. No. 4,832,488 and DE 2800225 A1. Such methods, however, do not provide teachings relating to verifying usability of a test strip.

Taking into account the state of the art, an object of the present invention is to provide a simple and reliable method for verifying the usability of test elements in an analysis system. This object, and other objects that will be apparent from this disclosure to those of skill in the art, may be achieved by one or more of the embodiments disclosed and claimed herein for the present invention.

SUMMARY

In one embodiment of the method according to the present invention, verification of the usability of a test element is performed by determining whether a measured value for at least one control parameter measurable from a test element is within a pre-determined tolerance range. Such a determination may comprise the following steps:

a) Determining a first standard value for the at least one control parameter measured from a standard reference, the standard reference providing a standardized reference value for the at least one control parameter;

b) Determining a reference value for the at least one control parameter from a first test element;

c) Calculating a first ratio from the reference value and the first standard value;

d) Determining a control value for the at least one control parameter from a second test element;

e) Calculating a second ratio from the control value and the first standard value; and f) Determining a deviation between the second ratio and the first ratio.

In such a determination, the second test element is rejected if the deviation from step (f) is not within a pre-determined tolerance range for the deviation.

While the present invention is generally described in the context of photometrically evaluated test elements, this disclosure is not intended to limit the universality of the application of the present invention to other types of test elements, e.g. electrochemical test elements. For example, for electrochemical test element systems, an electrically measured quantity indicative of the performance of the verification of usability of the test elements can be used. In one embodiment, a blank-field value measurement with an AC voltage, for which the impedance of phase shift comprise the control parameter, can be such a measured quantity. Other possible control parameters include conductivity, capacitance, inductance, decay times, frequency dependencies, and other functional correlations of electrically measured quantities which can be expressed in characteristic curves (e.g. a characteristic that depends on current, voltage or frequency). In other embodiments, in which the proper electrochemical test element itself does not provide or allow for measurement of a suitable control parameter, it is possible to add an additional component to the test element that provides a characteristic that allows measurement and which is appropriate for the usability verification method according to the present invention.

In any event, despite the specific optical system context of the following disclosure, analogous aspects can be found in electrochemical systems without departing from the overall scope of the present invention.

In an embodiment of the present invention, set forth here in the context of optical systems, the method generally comprises two aspects. According to the first aspect, the optical measurement system is itself monitored with regard to measurement variations. Typically, a standard value is measured from a standard reference, i.e. using a standardized optical reference surface, e.g. a white standard measurement, providing a standard value for a selected control parameter, such as remission. For this aspect, no sample fluid is applied to the standard reference surface.

Generally, this first standard value determines the current state of the evaluation device, e.g. the optical measurement system, and can be used also for a post-calibration of the device (although this is not necessary in the context of the present invention as it is sufficient to use the first standard value as a reference value for subsequent measurements).

According to the second aspect, the usability of individual test elements is verified. For this, the control parameter (e.g. remission) of a first test element is determined at the test field before a sample is applied thereto (i.e. a blank test field). For purposes of this disclosure, a test field is the portion of the test element where a characteristic reaction takes place when a sample fluid is applied. The control parameter determination for a blank test field of the first test element comprises a reference value against which subsequent test elements are verified. For this purpose, a first ratio is calculated from the reference value from the first test element and the first standard value (from the standardized optical reference surface). The usability of a second test element (and subsequent test elements) is verified by determining the control parameter at the blank test field of the second test element (which determination is designated as a control value), and a second ratio is calculated from the control value and the first standard value. The deviation between the second ratio and the first ratio is determined and compared against a pre-determined tolerance range. If the deviation is within the range, the second test element is verified as usable; if the deviation is not within the range, it should be rejected.

Using embodiments of the method of the present invention, it is possible to easily and reliably verify the usability of a test element before performing an analysis, without expensive re-calibration processes.

Using the embodiments of the method of the present invention presupposes that the first test element, which is used to determine the reference value from which is calculated the first ratio (along with the first standard value), is usable. That is, the usability of the first test element is not actually verified according to the present invention. However, this can be verified, at least in a rough manner, according to methods known in the state of the art, e.g. measuring the blank test field value for the control parameter and verifying that it is within a given tolerance for such a blank test field value.

In other embodiments, step (a) as described above is not needed. However, step (a) generally makes the embodiments of the present method more sensitive because it takes into consideration the differences between different evaluation devices, such as deviations due to manufacturing tolerances of the optical measuring systems.

The presupposition that the first test element is usable is generally inconsequential with regard to use of the present method in connection with a plurality of test elements provided in a package or other common storage container holding several similar test elements and having a long-term packaging that is common to all test elements. As a result, the common long-term packaging helps to ensure, with a high degree of safety, that the test elements contained therein, particularly the first test element, are usable at the time the packaging is opened, e.g. not deteriorated, except for possible deterioration caused by temperature influences which can be determined by means of known blank value tolerance measurement techniques. After opening the long-term packaging, however, the danger of damage to individual test elements is higher. It is in this regard that the embodiments of the present invention can be useful for verifying the usability of test elements well after the long-term packaging has been opened.

Embodiments of the present invention enable a simple and reliable verification, and one or more of the method steps can be performed automatically, i.e. in a user-independent way. Moreover, the sequence of steps as described above and in more detail below can be easily and conveniently re-ordered; e.g., steps (a) and (b) can be reversed, etc. Thus, any designation of 'first' step, etc. is only for purposes of designating and differentiating the individual steps without necessarily determining the actual sequence.

Furthermore, the terms "first test element" and "second test element" do not restrictively designate the first measured test element of a package or immediately subsequent test element, respectively, but rather designate merely a conceptual differentiation. The first test element is the one used for determining the reference value, and is typically but not necessarily the first test element from a given package or container. Similarly, the second test element is merely a test element that undergoes usability verification subsequently and in relation to the first test element, and can include all test elements following the first test element.

The embodiments of the present invention will subsequently be explained in detail with the help of an exemplary embodiment shown in the figures. The characteristics described can be used individually or in combination, in order to create various embodiments of the present invention.

BRIEF DESCRIPTION OF THE DRAWINGS

Further features and advantages of the present invention will become apparent from the following discussion and the accompanying drawings in which.

Skilled artisans appreciate that elements in the figures are illustrated for simplicity and clarity and have not necessarily been drawn to scale. For example, the dimensions of some of the elements in the figure may be exaggerated relative to other elements to help improve understanding of the embodiment(s) of the present invention.

In order that the present invention may be more readily understood, reference is made to the following examples, which are intended to illustrate the present invention, but not limit the scope thereof.

DETAILED DESCRIPTION OF EMBODIMENTS OF THE PRESENT INVENTION

The following description of the preferred embodiment is merely exemplary in nature and is in no way intended to limit the present invention or its application or uses.

Figure 1:
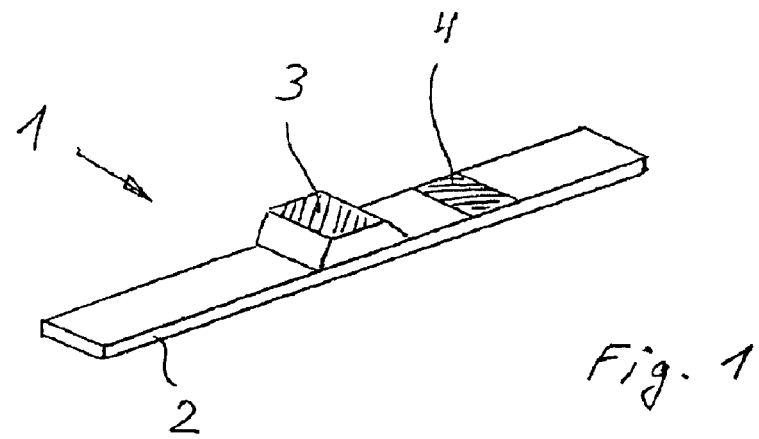
FIG. 1 shows an analysis element in the shape of a test strip.

FIG. 1 shows an embodiment of a test element 1 configured as a test strip which can be inserted into an evaluation device (not shown). An evaluation device and corresponding test elements comprise an analysis system. A test element 1 generally comprises a flexible, resilient base layer 2, typically comprising a plastic material. Base layer 2 supports a test field 3, onto which a sample fluid to be analyzed is applied. During analysis, characteristic chemical reactions take place between the sample fluid and the reagent contained in the test field 3. For an optical system, a resulting, optically detectable change can be evaluated, such as by reflection photometry.

As mentioned previously, various embodiments of test elements 1 are known, differentiated, for example, by the type of chemical detection reaction, the configuration of the test field 3, the measurement method, and the number of different test fields 3 on the test element 1. Generally, all test elements known in the art are appropriate for the embodiments of the present invention disclosed herein.

A rough check of the usability of a test element 1 can be done by a so-called blank field (or dry blank) value measurement, i.e. a measurement of the test field 3 without applying a sample fluid. For this, the test element 1 is provided to the evaluation device without first applying a sample fluid, and the blank field value is measured. If the blank field value is within a given tolerance range, it is likely sufficiently usable for purposes of the present invention. The blank field value from a first test element 1 serves as a reference value with respect to a control parameter of interest in the embodiments of the present invention. Further, the tolerance range of the blank field value may be pre-determined based on batch- or lot-specific information for the test element 1.

Subsequently, the test element 1 is removed from the evaluation device, sample fluid is applied to it, and it is then provided to the evaluation device again for performing a normal analysis. In one embodiment, the evaluation device is configured such that the sample can be applied without the need to first remove the test element 1 after the blank field measurement.

According to certain embodiments of the present invention, test element 1 further comprises means for an integrated standard reference 4 in addition to the test field 3, in order to provide a standardized reference value for the control parameter(s) selected for purposes of the present invention. In one embodiment, the remission measurement value comprises the at least one control parameter. The standard reference 4 does not undergo any chemical or other material or characteristic change as a result of application of the sample fluid to the test field 3. In other embodiments, the standard reference 4 is non-reactive with the sample and no sample adheres to it. In yet other embodiments, the standard reference 4 comprises a reference field configured to provide a standardized value for the control parameter, e.g. remission. In yet other embodiments, the standard reference 4 comprises or otherwise contains a white plastic foil.

In one embodiment, the remission value for the reference field is relatively high, e.g. 80%, in order to allow for higher measured remission values as the control parameter and thus a relatively high accuracy of measurement. Nevertheless, lower remission values are also useful in this regard and are considered within the scope of the present invention. For example, a less-remitting gray surface can be provided as the standard reference 4. Furthermore, the remission value of the standard reference 4 need not be stable over a long period of time. In other embodiments, however, the characteristics of the standard reference 4 are largely or entirely independent of environmental conditions such as temperature and humidity.

FIG. 1 shows the standard reference 4 as a reference field configured as part of the test element 1. In other embodiments, the standard reference 4 can be any portion of test element 1, e.g. a part of the surface of the plastic (such as a white plastic) comprising the base layer 2, rather than a particularly configured reference field. Thus, identification of a reference field in FIG. 1 also merely illustrates that some portion of the base layer 2 may serve as the standard reference 4 without specifically differentiating a particular portion as illustrated.

A reference field as shown for the standard reference 4 in FIG. 1 can be a component of test element 1, but in other embodiments a reference field may be provided on a separate reference test strip (not shown) that is not configured with a test field 3. Such a reference test strip may be provided with the evaluation device and/or with a package or other batch or lot of test elements 1.

In yet other embodiments, the standard reference 4 (including a reference field) can be an integrated component of the corresponding evaluation device itself.

Standard reference 4 provides a standard value for a control parameter relating to the current state of the evaluation device or its measurement system (e.g. optical system). In this way, the method of the present invention accounts for fluctuations of the measurement conditions caused by the device itself. Thus, one embodiment of the present invention comprises measuring a first standard value from the standard reference 4 (e.g. a reference field), such as a white standard value W1 of, e.g., about 80% remission. In other embodiments, the test element 1 is positioned within the evaluation device in such a way as to measure remission at the reference field rather than at the test field 3.

White standard value W1 typically results in a fixed and constant value only for particular evaluation devices having defined and generally constant measuring properties. However, this cannot be realized in practice generally, particularly for devices in use by non-expert users outside of laboratories. Thus, standard value W1 is useful for accounting for measurement fluctuations caused by the evaluation device and also possibly for measurement fluctuations relating to characteristics of the reference field. Indeed, certain embodiments of the present invention include aspects based on a first standard value, e.g. white value W1, in order to account for device-based fluctuations which can arise in the short term.

In one embodiment, blank-field reference value L1 from test field 3 of first test element 1 brought into the measuring position within the evaluation device is determined for the control parameter either after or before measurement of the first standard value, e.g. value W1. In other embodiments, the evaluation device may be configured to compare the reference value L1 to a given tolerance range. In other embodiments, the pre-determined tolerance range for a blank field reference value L1 presupposed to be from a usable first test element 1 is between about 55% and about 65%, with an actual ideal measured remission value of about 60%.

A first ratio Q1 is calculated and set for purposes of verifying usability of subsequent test elements 1. Ratio Q1 is calculated from the reference value L1 measured for the first test element 1 and the first standard value W1. In an exemplary embodiment using the exemplary values for W1 and L1 disclosed above, first ratio Q1 would be 60/80=0.75.

The first test element 1 may be used for performing an analysis on a sample fluid after it is used for calculating the first ratio Q1. Sample is either applied to the test field 3 of the test element 1 left in the evaluation device or the test element is removed, sample applied to the test field 3 of the test element 1, and the test element 1 is provided to the evaluation device again.

When a second test element 1 is to be used, its usability is verified relative to the first test element by determining a control value L2 for the control parameter, e.g. a blank field value from test field 3 of the second test element, and the value L2 is provided with the first standard value W1 to calculate the second ratio Q2. The deviation $\Delta$ between the second ratio Q2 and the first ratio Q1 is then determined and the second test element 1 is rejected if the deviation $\Delta$ is not within a pre-determined tolerance range for such deviation.

The deviation $\Delta$ can comprise any useful computation relating ratios Q1 and Q2 for purposes of determining whether the deviation $\Delta$ is within or outside a particular tolerance range. In one embodiment, deviation $\Delta$ comprises ratio Q1/Q2 or Q2/Q1, illustrating a relative different between the first ratio Q1 and the second ratio Q2. In other embodiments, deviation $\Delta$ comprises an absolute difference Q1−Q2. In yet other embodiments, deviation $\Delta$ comprises a functional or parametrical evaluation for illustrating the difference between Q1 and Q2.

For example, if the blank-field control value L2 is 56.4%, and the tolerance range for the admissible deviation is a relative $\Delta$ of 6% from the first ratio Q1, or absolute difference between them or 0.045, then the second ratio Q2, calculated to be 56.4/80=0.705, is just within the admissible range, which verifies the usability of the second test element. However, if the blank field control value L2 is 50% with the same tolerance ranges, second ratio Q2 is 50/80=0.625, which gives a relative deviation $\Delta$ of 16% and an absolute difference of 0.125. In that case, the second test element is outside of the tolerance range and should be rejected from use.

In one embodiment, tolerance ranges for an admissible deviation $\Delta$ can be batch-specific for the batch of test elements from which the first and second test elements are provided. Such ranges can be provided by or on the test elements themselves or on their packaging, such as by a bar code, which can be read by the evaluation device for use in the verification determination and the measurement analysis. In other embodiments, a set of tolerance ranges is stored in the evaluation device, and the bar code or other indicator from the test element or the packaging indicates the range value(s) for that particular batch or lot in question.

In other embodiments, measurement of the first standard value W1 can be performed for each test element. In yet other embodiments, the first standard value W1 is determined only at the time of use of the first test element or as otherwise necessary, in order to save time in the overall measurement sequence.

In certain embodiments, particularly analysis systems for qualitative or quantitative analysis of components of a solid or liquid sample, such as biological fluids from human beings and other animals (including determination of blood glucose concentration), a second test element may be rejected as not usable if the second ratio Q2 is smaller than the first ratio Q1 by more than a certain percentage or more than a certain absolute difference value. In this regard, it has been found that in the context of blood glucose concentration determinations, the effects of aging and deterioration lead to decreases in remission values and thus to a decrease of second ratio Q2 such that certain benchmark differences can be useful.

In yet another embodiment, in particular for the test elements mentioned above, if the deviation $\Delta$ indicates a certain characteristic relation of Q1 and Q2, then control value L2 may be used as new reference value L1 for subsequent uses of the method, and a new ratio Q1 is calculated from this. Essentially, this means that ratio Q2 is re-assigned as new ratio Q1. This new ratio Q1 is then used as a basis for verifying usability of subsequent test elements. In this regard, a characteristic relation of Q1 and Q2 that might lead to the replacement of the first ratio Q1 by the later measured second ratio Q2 for purposes of subsequent verifications, can be the observation that the second ratio Q2 exceeds the current (first) ratio Q1 by more than a pre-determined limit value $\delta$.

For example, in one embodiment a pre-determined limit value δ may be set as 3% relative difference between Q1 and Q2 or 0.0225 absolute difference. If the measurement of the control value L2 of second test element is more than 61.8%, then second ratio Q2 is bigger than 0.7725, and thus the first ratio Q1 (which was calculated to be 0.75) is replaced by the second ratio Q2. In other embodiments, the limit value δ can be batch-specific for the current batch of the test elements from which the test elements are provided.

It has further been found that an increase of the second ratio Q2 as compared to the first ratio Q1 may result, in embodiments in which an optical measurement system has been cleaned, or if any other action has been taken which may influence the analysis system. Fortunately, this effect can be determined as a result of using the method according to the present invention and thus taken into account when verifying the usability of the test elements.

It should be noted that in the examples set forth above and below, ratios and differences can be calculated in either order as desired, i.e. with commuted dividend and divisor, or with commuted minuend and subtrahend.

Figure 2:
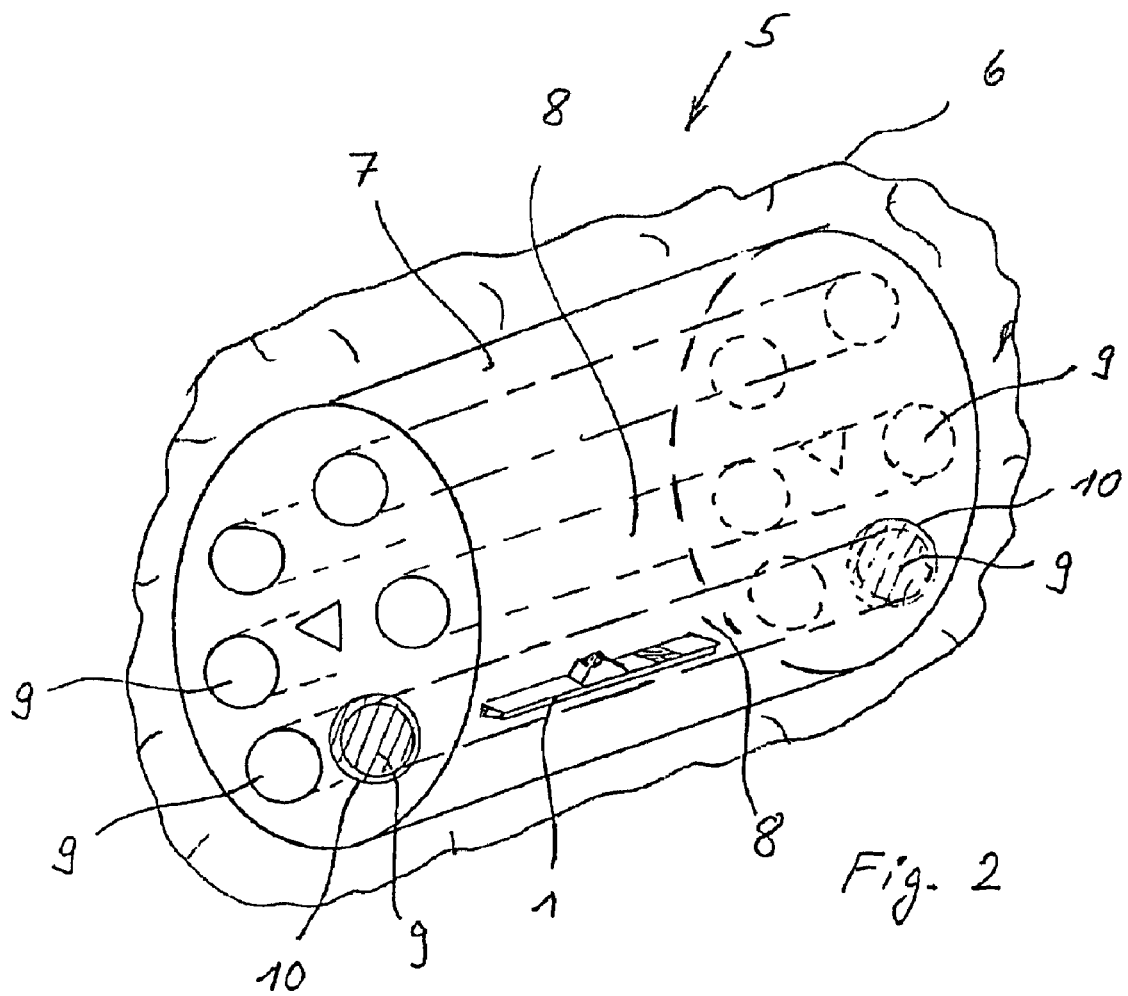
FIG. 2 shows a package with test strips contained in a storage container.

Typical embodiments of the method according to the present invention are used for verifying the usability of test elements that are supplied to users in a common package or storage container such that first and second test elements are subject to long-term packaging effects common to all test elements. FIG. 2 schematically shows one embodiment of such a package 5 with a test element 1 contained therein shown schematically. As shown, test elements provided in a package 5 are enveloped by a long-term packaging 6, configured to provide relatively safe protection. In certain embodiments, the long-term packaging 6 comprises high-tenacity welded foil, or a tube-shaped container made of plastic or metal, e.g. aluminium.

In one embodiment, each of the test elements 1 contained in the package 5 may be protected by an individual packaging element (such as a desiccant). As shown, the packaging 6 ensures relatively secure storage over a long period of time, or at least secure transport. In order to use the test elements 1 contained in package 5, a user first opens the packaging 6 and the test elements 1 contained therein are then consumed one by one. In the time between the opening of the packaging 6 and the use of any certain test element 1, the individual packaging elements ensure the required minimum protection. In other embodiments, the method according to the present invention allows a user to verify whether the minimum protection has actually been provided, and whether all test elements 1 (or any individual test element) have deteriorated with respect to their usability after the opening of the long-term packaging 6.

It is generally known in the art to provide test elements 1 in long-term packaging 6 not in a loose way but in a storage container 7 which not only functions as a package, but which is also a functional part of the analysis system during use of the test elements 1. The arrangement of various storage containers 7 in a common packaging 6 is also possible. Examples for such storage containers and removal devices can be found in the documents DE 19854316 A1, EP 1022565 A2, U.S. Pat. No. 4,615,462, U.S. Pat. No. 4,834,234, U.S. Pat. No. 5,645,798 and U.S. Pat. No. 5,720,924.

In an exemplary embodiment, FIG. 2 shows a storage container 7 in the form of a magazine, having a plurality of chambers 8 configured to hold the test elements 1. The openings 9 of the chamber 8 are closed by sealing foils 10 which correspondingly comprise individual packaging units. The sealing foils 10 are punctured in order to remove test element 1 from a chamber 8 in the storage container 7. For test elements 1 remaining in their respective chambers 8 in the storage container 7, the sealing foils 10 are kept intact in order to maintain protection for them.

By way of example, storage container 7, illustrated in FIG. 2 in the shape of a magazine, is configured for use in an evaluation device. Corresponding means for the exact positioning and removal can be provided in order to incorporate a storage container 7 into an evaluation device, including means for removing a test element 1 from a chamber 8, such as by a plunger.

According to certain embodiments of the present invention, it is supposed that the test elements 1 are usable at least until the long-term packaging 6 is opened, or that potential deterioration, e.g. as a result of temperature extremes which affect all test elements 1, can be detected using a conventional checking method. Typically in use, long-term packaging 6 is not opened until immediately before the first use of an test element 1 contained therein. Thus, according to one embodiment of the present invention, the determination of the reference value L1 is performed on the first test element 1 removed from a package 5 (or a storage container 7 contained in package 5). In other embodiments, the evaluation device is configured to automatically determine the first standard value W1 and the reference value L1 and to calculate the first ratio Q1, either whenever a new package 5 is used, whenever a first analysis element 1 of a package 5 or a storage container 7 is used, or whenever long-term packaging 6 is first opened.

In yet other embodiments, the steps of determining W1 and L1 and calculating Q1 are repeated (either automatically by the evaluation device or at the instruction of a user) whenever the analysis system experiences anything that could influence the measurement of the control parameter by the evaluation device, e.g. a cleaning of the optical system. For example, a performance of those steps can be activated automatically if the evaluation device registers, such as by a control switch, that a cover of the evaluation device which enables access to the optical system was opened, which would indicate that a cleaning process has probably been performed.

The subsequent Tables 1 and 2 show the results of practical trials of an embodiment of the present invention. During the trials, test strips configured for determination of concentration of blood glucose were used. The test strips suffered artificial aging by submitting them to 80% relative humidity. For this, the high humidity serves to enhance stress on the strip, thereby accelerating the aging processes. Corresponding trial results were obtained from test strips stressed by increased temperature, or test strips under real conditions with prolonged aging conditions.

Table 1 displays the stress results for 80% relative humidity with a first, fixed standard reference value W1. The symbol 't' is the time duration of the humidity stress for 80% relative humidity, expressed in hours. The standard value W1 determined in step (a), the reference value L1 determined in step (b), and the control value L2 determined in step (d) are given arbitrarily in mV. In practice, other units may occur, too, e.g. mA, light intensity or a percentage of the remission value, depending on the particular control parameter selected. The first ratio Q1 calculated in step (c) and the second ratio Q2 calculated in step (e) are provided in percent. The last column of the table shows the deviation Δ between the second ratio Q2 and the first ratio Q1, determined in step (f). In this example, the difference of these values has been chosen.

It can be seen that as aging effects increase, the second ratio Q2 decreases with increasing stress time. The deviation Δ between the second ratio Q2 and the first ratio Q1 increases accordingly. If the determined deviation Δ exceeds a given limit value, it is possible to determine by this that the test element intended for an analysis is not usable. In Table 1, such a limit could be set for a Δ bigger than ±6, for example.

TABLE 1

Aging test for a relative humidity of 80% with a fixed standard value W1.

| t in h | a) W1 in mV | b) L1 in mV | c) Q1 = L1/W1 in % | d) L2 in mV | e) Q2 = L2/W1 in % | f) Δ = Q2 − Q1 |
|---|---|---|---|---|---|---|
| 0 | 88.5 | 67.6 | 76.4 | — | — | — |
| 48 | — | — | — | 65.8 | 74.4 | −2.0 |
| 96 | — | — | — | 60.3 | 68.1 | −8.3 |
| 144 | — | — | — | 56.7 | 64.1 | −12.3 |
| 192 | — | — | — | 53.4 | 60.3 | −16.1 |

Table 2 shows another test study similar to the study from Table 1, except that in Table 2 the standard value W1 is determined at the beginning and is determined again for every time-related control stage. A corresponding variation of the standard value W1 can also result from the fact that different evaluation devices are used, which can be different with respect to their measuring-technological characteristics, e.g. the optical systems.

In Table 2 it can also be seen that the variation of the standard value W1, included here only for test purposes, is low, because it is not subject to the aging process. Thus, during the practical use of the invention, it is not necessary to re-determine the standard values W1 each time, in order to identify aging effects indicated by the differences in the control values L2.

TABLE 2

Aging test for a relative humidity of 80% with change of standard value W1.

| t in h | a) W1 in mV | b) L1 in mV | c) Q1 = L1/W1 in % | d) L2 in mV | e) Q2 = L2/W1 in % | f) Δ = Q2 − Q1 |
|---|---|---|---|---|---|---|
| 0 | 88.5 | 67.6 | 76.4 | — | — | — |
| 48 | 88.1 | — | — | 65.8 | 74.7 | −1.7 |
| 96 | 87.8 | — | — | 60.3 | 68.7 | −7.7 |
| 144 | 88.2 | — | — | 56.7 | 64.3 | −12.1 |
| 192 | 88.3 | — | — | 53.4 | 60.5 | −15.9 |

The effects of aging with respect to the inaccuracy of the measurement results for the glucose concentration 'c' is shown in Table 3.

TABLE 3

Glucose values after aging

| c for t = 0 in mg/dl | t in h | c (t) in mg/dl | Δ c in % |
|---|---|---|---|
| 87.3 | 48 | 86.8 | −0.6 |
| 87.3 | 96 | 79.4 | −9.0 |
| 87.3 | 144 | 74.7 | −14.4 |
| 87.3 | 192 | 71.3 | −18.3 |
| 201.7 | 48 | 207.6 | 2.9 |
| 201.7 | 96 | 194.6 | −3.5 |
| 201.7 | 144 | 183.9 | −8.8 |
| 201.7 | 192 | 172.0 | −14.7 |
| 343.9 | 48 | 350.1 | 1.8 |
| 343.9 | 96 | 332.6 | −3.3 |
| 343.9 | 144 | 313.6 | −8.8 |
| 343.9 | 196 | 299.3 | −13.0 |
| 504.8 | 48 | 510.9 | 1.2 |
| 504.8 | 96 | 474.8 | −5.9 |
| 504.8 | 144 | 446.2 | −11.6 |
| 504.8 | 196 | 422.4 | −16.3 |

Results show that for test strips stressed at 80% relative humidity for at least 96 hours, deviations in actual glucose concentration can reach over 5% at the higher concentrations. If a tolerance range for the deviation Δ of ±6 is chosen accordingly for the Tables 1 and 2, the aged test elements which are no longer usable can be identified and segregated, using the embodiments of the method according to the present invention.

The method according to the invention offers advances over the state of the art, for which the control value is only compared to a fixed limit value, pre-adjusted on the evaluation device. The differentiation potential according to the state of the art is essentially lower, so that, for example, glucose value deviations between stressed and unstressed samples can only be recognised if they correspond to 30% or more. Thus, the known methods cannot even determine the deviation of the glucose values of about 15%, occurring after a stress time of 192 hours (see Table 3).

The embodiments of the present invention provide a simple and reliable verification of the usability of test elements. In one embodiment, the blank field values measured for determining the reference value and the control value are obtained automatically by the evaluation device for each test element. As has been pointed out above, the precision of the verification of usability and thus the results obtained by the analysis system are increased as a result of the present invention. Furthermore, the state of the measurement system of the evaluation device is taken into account, making the verification method independent of variations in the evaluation device. As described above, for optical systems, the evaluation device is referenced to a white standard, and the blank-field reference and control values of the test elements is also referenced to the white standard as a result of the calculation of the first ratio. The second ratio for a test element is compared to the first ratio. The first ratio is updated in case of necessity, so that the real state of the optical system of the evaluation device and any batch-dependent target value for a package of test elements are always taken into account during each verification process. By this, a very fine recognition characteristic for deteriorated test elements is obtained.

To check the effectiveness of the method of the present invention, a user could attempt to use a series of stressed and unstressed test elements in a corresponding evaluation device and in an alternating fashion, thus testing the reaction of the evaluation device in rejecting unusable test elements (the stressed test elements) and continuing with the analysis (or other measurement functionality according to the evaluation device) on the unstressed strips.

The features disclosed in the above description, the claims and the drawing may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A method for verifying the usability of a test element provided for use with a corresponding evaluation unit for analysis of a liquid sample, the method comprising the steps of:
    a) determining a first standard value (W1) for at least one control parameter measured from a standard reference presented to the evaluation unit, the standard reference providing a standardized reference value (W1) for the at least one control parameter;
    b) providing a first test element comprising a first test field to the evaluation device and determining a blank-field reference value (L1) for the at least one control parameter from the first test field);
    c) calculating a first ratio (Q1=L1/W1 or W1/L1) from the reference value (L1) and the first standard value (W1);
    d) providing a second test element comprising a second test field to the evaluation device and determining a blank-field control value (L2) for the at least one control parameter from the second test field;
    e) calculating a second ratio (Q2=L2/W1 or W1/L2) from the control value (L2) and the first standard value (W1);
    f) determining a deviation ($\Delta$) between the second ratio (Q2=L2/W1 or W1/L2) and the first ratio (Q1=L1/W1 or W1/L1); and
    g) rejecting the second test element if the deviation ($\Delta$) is not within a pre-determined tolerance range for the deviation ($\Delta$).

2. The method according to claim 1, wherein determining the deviation ($\Delta$) comprises calculating a relative difference ($\delta$) between the second ratio (Q2=L2/W1 or W1/L2) and the first ratio (Q1=L1/W1 or W1/L1).

3. The method according to claim 1, wherein determining the deviation ($\Delta$) comprises calculating an absolute difference (Q1−Q2 or Q2−Q1) between the second ratio (Q2=L2/W1 or W1/L2) and the first ratio (Q1=L1/W1 or W1/L1).

4. The method according to claim 1, wherein the rejecting step comprises rejecting the second analysis element if the second ratio (Q2=L2/W1 or W1/L2) is smaller than the first ratio (Q1=L1/W1 or W1/L1) by at least a pre-determined percentage.

5. The method according of claim 1, wherein the rejecting step comprises rejecting the second analysis element if the second ratio (Q2=L2/W1 or W1/L2) is smaller than the first ratio (Q1=L1/W1 or W1/L1) by at least a pre-determined absolute difference value (Q1−Q2 or Q2−Q1).

6. The method according to claim 1, wherein the at least one control parameter is an optically measurable value.

7. The method according to claim 6, wherein the optically measurable value comprises a remission value.

8. The method according to claim 1, wherein the first pre-determined tolerance range for the deviation ($\Delta$) is determined with respect to a batch of test elements from which the first and second test elements are provided.

9. The method according to claim 1, further comprising calculating a new ratio from the control value (L2) and the first standard value (W1).

10. The method according to claim 1, wherein the first test element and the second test element are provided after being removed from a container configured for substantially preventing deterioration of the first test element and the second test element.

11. The method according to claim 10, wherein the first test element is provided to the evaluation device before the second test element.

12. The method according to claim 1, further comprising the steps of:
    h) re-assigning the second ratio (Q2=L2/W1 or W1/L2) as a new first ratio (Q1=L1/W1 or W1/L1);
    i) providing a third test element having a third test field to the evaluation device and determining a new blank-field control value (L2) for the at least one control parameter from the third test field;
    j) calculating a third ratio (Q2=W1/L2 or L2/W1) from the new control value (L2) and the first standard value (W1);
    k) determining a deviation ($\Delta$) between the third ratio (Q2=W1/L2 or L2/W1) and the new first ratio (Q1=L1/W1 or W1/L1); and
    l) rejecting the third test element if the deviation ($\Delta$) determined from step (k) is not within the pre-determined tolerance range for the deviation ($\Delta$).

13. The method according to claim 12, further comprising the steps of determining whether the deviation ($\Delta$) determined from step (f) exceeds a pre-determined limit value ($\delta$), wherein step (h) is not performed if the determination shows the deviation determined from step (f) does exceed the pre-determined limit value ($\delta$), and wherein if step (h) is not performed then step (k) comprises determining a deviation ($\Delta$) between the third ratio (Q2=W1/L2 or L2/W1) and the first ratio (Q1=L1/W1 or W1/L1).

14. The method according to claim 13, wherein the pre-determined limit value ($\delta$) is determined with respect to a batch of test elements from which the first, second and third test elements are provided.

* * * * *